(12) United States Patent
Toki et al.

(10) Patent No.: US 7,786,331 B2
(45) Date of Patent: Aug. 31, 2010

(54) FRAGRANCE COMPOSITION

(75) Inventors: Naotoshi Toki, Wakayama (JP); Kosaku Ishida, Wakayama (JP); Kazuyuki Fukuda, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/539,257

(22) Filed: Aug. 11, 2009

(65) Prior Publication Data

US 2010/0010275 A1 Jan. 14, 2010

Related U.S. Application Data

(62) Division of application No. 11/911,751, filed as application No. PCT/JP2006/313015 on Jun. 29, 2006, now Pat. No. 7,648,956.

(30) Foreign Application Priority Data

Jun. 29, 2005 (JP) ............................ 2005-189328
Mar. 31, 2006 (JP) ............................ 2006-096628

(51) Int. Cl.
*C07C 35/00* (2006.01)
*A61K 8/18* (2006.01)

(52) U.S. Cl. ........................................ 568/819; 512/17

(58) Field of Classification Search .................... 512/17, 512/1; 568/819
See application file for complete search history.

(56) References Cited

U.S. PATENT DOCUMENTS

2009/0123404 A1  5/2009  Fukuda et al.

OTHER PUBLICATIONS

Ohloff et al. Croatica Chemica Acta vol. 58 No. 4 pp. 491-509 1985.*
Andrews et al. J. Org. Chem. vol. 54 No. 22 pp. 5257-5264.*

Corbier, et al., "New Components from French Tobacco Absolute (*Nicotiana tabacum*)", Flavors and Fragrances: A World Perspective, pp. 483-494, 1988.

Ohloff, et al., "Structure-Activity Relationships in Odor Perception of Drimane Derivatives", Croatica Chemica Acta, vol. 58, No. 4, pp. 491-509, 1985.

Wahlberg, et al., "Tobacco Chemistry. 53. Two New Nor-Drimanes from Greek Tobacco", Acta Chemica Scandinavica Series B Organic Chemistry and Biochemistry, vol. 35, No. 4, pp. 307-310, 1981.

Andrews, et al., "Decarbonylation of Unprotected Aldose Sugars by Chlorotris(triphenylphosphine)rhodium(I). A New Descent of Series Approach to Alditols, Deoxyalditols, and Glycosylalditols", Journal of Organic Chemistry, vol. 54, No. 22, pp. 5257-5264, 1989.

* cited by examiner

*Primary Examiner*—Milton I Cano
*Assistant Examiner*—Aaron Greso
(74) *Attorney, Agent, or Firm*—Oblon, Spivak, McClelland, Maier & Neustadt, L.L.P.

(57) ABSTRACT

A method of making a decalin alcohol; the alcohol is applied as a component in a fragrance composition containing 0.0005 to 10% by mass as component (a), represented by formula (1a), and 90 to 99.9995% by mass of one or more polycyclic woody-amber fragrances as component (b) selected from the group consisting of 7-acetyl-1,2,3,4,5,6,7,8-octahydro-1,1,6,7-tetramethylnaphthalene; 1,2,3,4,4a,5,6,7-octahydro-2,5,5-trimethyl-2-naphthalenol; 1,2,3,4,4a,7,8,8a-octahydro-2,4a,5,8a-tetramethyl-1-naphthyl formate; 3a-ethyl-dodecahydro-6,6,9a-trimethylnaphtho[2,1-b]furan; and racemic or optically active dodecahydro-3a,6,6,9a-tetramethylnaphtho[2,1-b]furan; the fragrance composition being contained in a cosmetic product, a household product, and an environmental/sanitary product. The fragrance composition of the present invention is a highly versatile fragrance composition that, with the decalin alcohol, brings about an odor of natural ambergris with an odor quality that imparts the effects of warmth even when employed in a small amount.

18 Claims, No Drawings

FRAGRANCE COMPOSITION

CROSS REFERENCES TO RELATED APPLICATIONS

This application is filed as a division of U.S. patent application Ser. No. 11/911,751, filed on Oct. 17, 2007, now U.S. Pat. No. 7,648,956, issued Jan. 19, 2010, which is a 371 of International Patent Application No. PCT/JP2006/313015, filed on Jun. 29, 2006, and claims priority to Japanese Patent Application No. 2005-189328, filed on Jun. 29, 2005 and Japanese Patent Application No. 2006-096628, filed on Mar. 31, 2006.

TECHNICAL FIELD

The present invention relates to a fragrance composition containing a decalin alcohol having a specific structure.

BACKGROUND ART

Recently, both in Japan and in other countries, as lifestyle varies, the affluence and pleasure and the approach to and effect on emotion brought about by fragrance have attracted attention as factors to improve the life quality. At the same time, there has been demanded development of fragrances that are highly safe and can attain highly significant effects when mixing small amounts in view of the burden on the environment.

Synthetic fragrances having a polycyclic structure and a woody and amber-like odor have been known to bring about a odor reminiscent of natural wood or ambergris and additionally to effectively persist, even with small applied amounts, on various objects such as the skin, hair and clothes so as to enhance the value thereof from the viewpoints of both preference and functionality.

Typical examples of such synthetic fragrances include acetyl cedrene, isolongifolanone and cedryl methyl ether; however, all these are prepared by using natural wood as raw materials, and hence excessive logging causes various environmental problems such as flood. Accordingly, demand for synthetic fragrances prepared by using raw materials other than wood has increased.

G. Ohloff et al. have long paid attention to the decalin skeleton in relation to compounds having a polycyclic structure, and have reported that 9-nordrimanol having four methyl groups develops an odor most resembling that of amber on the basis of a synthetic study on decalin alcohols substituted with many methyl groups; however, decalin alcohols substituted with five or more methyl groups or decalin alcohols with ethyl groups introduced thereinto are odorless, or have created no interest (Non-patent Document 1). Additionally, no industrial production method has yet been developed for any of these compounds, and none of these compounds has so far been utilized as a fragrance.

Additionally, 1,2,3,4,4a,5,6,7-octahydro-2,5,5-trimethyl-2-naphthalenol having an octalin skeleton similar to that of decalin skeleton and hydroxy groups, and having been used as a fragrance smells strong and hence can display its effect in a small mixing amount; however, this compound has a strong animalic odor and hence has a drawback of being poor in general versatility.

Similarly, 7-acetyl-1,2,3,4,5,6,7,8-octahydro-1,1,6,7-tetramethylnaphthalene having an octalin skeleton and an acetyl group and being prepared from myrcene, a natural raw material, has general versatility, but gives out a rough and dry smell, and hence has a drawback that such features of this compound are hardly compatible with fragrances such as perfumes required to have a high quality and an impression of being differentiated.

On the other hand, 8-drimanol having a steric structure represented by formula (1a) was not studied in the study of fragrance compounds having a decalin skeleton carried out by G. Ohloff et al.; in Non-patent Document 1, (9βH)-driman-8β-ol having a different steric structure has been reported to be odorless, but no additional description on the odor of driman-8β-ol is found therein.

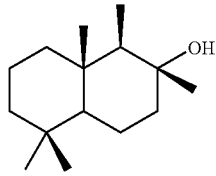

(1a)

Additionally, J. R. Hlubucek found that *Nicotiana tabacum* L. in Greek tobacco contains the compound represented by formula (1a), and tried to prepare the compound represented by formula (1a) from drim-7-en-11-ol, but the odor of the prepared compound was not described and the importance thereof as a fragrance has not been known (Non-patent Document 2).

C. R. Enzell obtained a mixture containing 8-drimanol through a bioconversion of (z)-abienol, but no description is found on the aspect of this mixture as a fragrance (Non-patent Document 3).

[Non-patent Document 1] Croatica Chemica Acta, 58(4), p. 491 (1985)

[Non-patent Document 2] Acta Chemica Scandinavica, B 28, No. 3 p. 289 (1974)

[Non-patent Document 3] Acta Chemica Scandinavica, 49, p. 375 (1995)

DISCLOSURE OF THE INVENTION

The present invention provides a fragrance composition including 0.0005 to 10% by mass of 8-drimanol [component (a)] represented by formula (1a) and 90 to 99.9995% by mass of one or more polycyclic woody-amber fragrances [component (b)] selected from the group consisting of 7-acetyl-1,2,3,4,5,6,7,8-octahydro-1,1,6,7-tetramethylnaphthalene, 1,2,3,4,4a,5,6,7-octahydro-2,5,5-trimethyl-2-naphthalenol, 1,2,3,4,4a,7,8,8a-octahydro-2,4-a,5,8a-tetramethyl-1-naphthyl formate, 3a-ethyldodecahydro-6,6,9a-trimethylnaphtho[2,1-b]furan, and racemic or optically active dodecahydro-3a,6,6,9a-tetramethylnaphtho[2,1-b]furan.

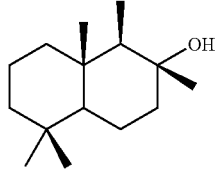

(1a)

Further, the present invention provides cosmetic products, household products and environmental/sanitary products including the above-mentioned fragrance composition.

Further, the present invention provides a method for improving the odor of a fragrance composition by adding the component (a) to the fragrance composition including the component (b).

Further, the present invention provides a method for producing a decalin alcohol (1) by subjecting a hemiacetal (2) or an aldehyde (3) to a decarbonylation reaction.

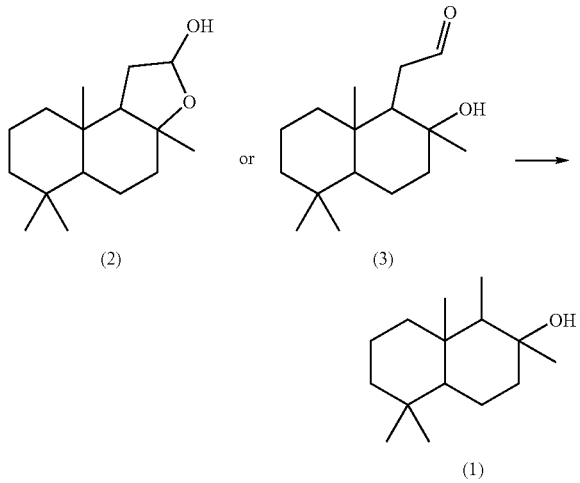

MODES FOR CARRYING OUT THE INVENTION

The present invention relates to a highly versatile fragrance composition that brings about an odor of natural ambergris and can attain effects to enhance warmth and an odor quality even in small amounts.

The present inventors have found that 8-drimanol, represented by the above formula (1a) and having never been found to be applicable as a fragrance, is characterized in that 8-drimanol emits a strong amber odor when heated although 8-drimanol itself has a weak woody-amber-like odor.

Further, the present inventors have found that the combination of 8-drimanol with a specific polycyclic woody-amber fragrance can enhance the odor, bring about such softness and warmth as possessed by natural ambergris, and consequently can attain an effect leading to a high quality improvement. Further, the present inventors have found that when a fragrance composition including 8-drimanol and a specific woody-amber fragrance compound is used for cosmetic products, household products and the like, the above-mentioned composition is characterized in that the composition imparts a pleasant amber-like lasting odor to the skin or the hair having been applied with the composition.

8-Drimanol as the component (a) included in the fragrance composition of the present invention is a compound that emits only a weak woody-amber-like odor at room temperature, but increases the odor intensity thereof steeply by heating to develop a pleasant amber-like odor. When combined with a specific fragrance [the component (b)] having a woody-amber-like odor, the component (a) attains an effect to enhance the amber-like odor and to impart and promote a voluminous and high odor quality, and makes it possible to obtain a fragrance composition having the same softness and warmth as those of natural ambergris. In other words, by adding the component (a) to a fragrance composition including a specific fragrance compound [the component (b)] having a woody-amber odor, the odor of the fragrance composition can also be improved.

As the method for producing 8-drimanol (1a), the above-mentioned method is known in which drim-7-en-11-ol is used as a raw material (Non-patent Document 2); however, this method uses a compound not easily available as a starting material, and additionally requires 6 steps. Accordingly, 8-drimanol (1a) is preferably produced by the method for producing the decalin alcohol (1) based on the decarbonylation reaction, represented by the following reaction formula, of hemiacetal (2) or aldehyde (3). According to this method, decalin alcohol (1) can be efficiently produced through a smaller number of steps.

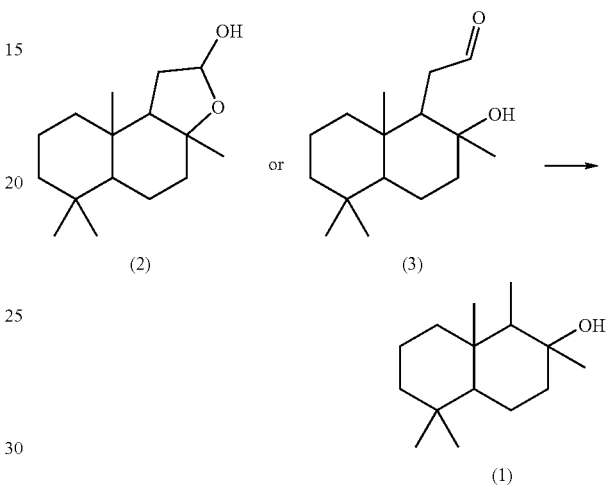

Conversion from Hemiacetal (2) or Aldehyde (3) to Decalin Alcohol (1)

The method for producing decalin alcohol (1), according to the present invention, based on the decarbonylation reaction of hemiacetal (2) or aldehyde (3) can be carried out by reacting these compounds by using a transition metal complex. Hemiacetal (2) and aldehyde (3) may be used each alone or as a mixture thereof.

As the transition metal complex, rhodium complexes, ruthenium complexes and iron complexes are preferable; rhodium complexes are more preferable. Of these, halotris (triphenylphosphine)rhodium(I), and halocarbonylbis(triphenylphosphine)rhodium(I) are preferable; chlorotris(triphenylphosphine)rhodium(I); [RhCl(PPh$_3$)$_3$], chlorocarbonylbis(triphenylphosphine)rhodium(I); [RhCl(CO)(PPh$_3$)$_2$], and the like are more preferable.

The transition metal complex is used preferably in an amount of 1 to 20 moles, more preferably 1 to 2 moles, based on 1 mol of the total amount of hemiacetal (2) and aldehyde (3).

Additionally, by adding an appropriate amount of a bidentate phosphine ligand to the rhodium complex, the amount of the rhodium complex used can be drastically reduced, and accordingly the reaction can be made possible with a catalytic amount of the complex. Examples of the used bidentate phosphine ligand include 1,2-bis(diphenylphosphino)ethane, 1,3-bis(diphenylphosphino)propane and 1,4-bis(diphenylphosphino)butane; particularly useful is 1,3-bis(diphenylphosphino)propane.

When a bidentate phosphine ligand is added, the addition amount of the bidentate phosphine ligand is 1 to 50 moles, more preferably 1 to 4 moles, based on 1 mole of the rhodium complex. In this case, the amount of the rhodium complex is appropriately 0.00001 to 1 mole, and preferably 0.001 to 0.05 mole from the viewpoints of economy and productivity, based on the 1 mole of the total amount of hemiacetal (2) and aldehyde (3).

The rhodium complex and the bidentate phosphine ligand may be added intermittently in the course of the reaction. Additionally, the rhodium complex and the bidentate phosphine ligand may be added separately, or the ligand may be coordinated with the rhodium complex before the addition.

As a reaction solvent, halogen-containing or aromatic solvents are preferable. For example, dichloromethane, benzene, toluene and xylene are preferable. In the reaction with a catalytic amount of the rhodium complex, xylene is more preferable because xylene is applicable to a high temperature reaction. The solvent amount is 1 to 100 mL, and preferably approximately 1 to 10 mL from the viewpoint of productivity, based on 1 g of the total amount of hemiacetal (2) and aldehyde (3).

In the atmosphere in which the transition metal complex is made to act on hemiacetal (2) or aldehyde (3), an inert gas such as a nitrogen gas or argon gas is preferably used. The reaction temperature is preferably set at temperatures exclusive of extremely high temperatures, and usually preferably set at 20 to 120° C. The reaction with a catalytic amount of the rhodium complex is a mode of reaction in which carbon monoxide is discharged outside the reaction system, and accordingly, the reaction is preferably carried out in a flow of nitrogen gas under reflux of the solvent, and hence the reaction temperature is preferably set at a temperature in the vicinity of the boiling point of the solvent.

The terminal point of the reaction can be set at the time at which hemiacetal (2) and aldehyde (3) vanish on the basis of gas chromatography, thin layer liquid chromatography or the like. The reaction time is usually 1 to 24 hours.

[Conversion from Sclareolide (4) to Hemiacetal (2) and Aldehyde (3)]

Additionally, hemiacetal (2) and aldehyde (3) used in the above-mentioned reaction can be produced by reducing sclareolide (4).

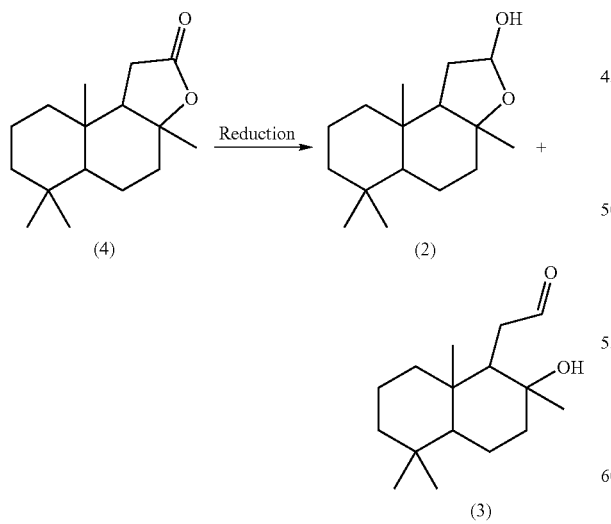

As the reducing agent, metal hydrides are preferable; aluminum hydride is more preferable. The amount of the reducing agent is preferably 0.1 to 5 moles, more preferably 0.5 to 2 moles, based on 1 mole of sclareolide (4).

As the solvent, those solvents having a low freezing point are preferable; for example, dichloromethane, hexane and toluene are preferable. Anhydrous solvents are more preferable.

The atmosphere in which a reducing agent is made to act on sclareolide (4) is preferably an atmosphere of an inert gas such as nitrogen gas or argon gas under anhydrous conditions. The reaction temperature is preferably set at low temperatures, more preferably set at −78° C. to −40° C.

The terminal point of the reaction can be set at the time at which sclareolide (4) vanishes on the basis of gas chromatography, thin layer liquid chromatography or the like. The reaction time is usually 30 minutes to 2 hours.

According to the method of the present invention, when (+)-sclareolide (4a) obtained by oxidizing (−)-sclareol, which is an extract obtained from natural clary sage, is used as sclareolide (4), 8-drimanol (1a) is obtained as decalin alcohol (1). 8-Drimanol (1a) has not been known to be usable as a fragrance; 8-drimanol (1a) emits only a weak amber odor at room temperature, but is characterized in that 8-drimanol (1a) emits a strong remarkable amber odor by heating at body temperatures to 50° C.

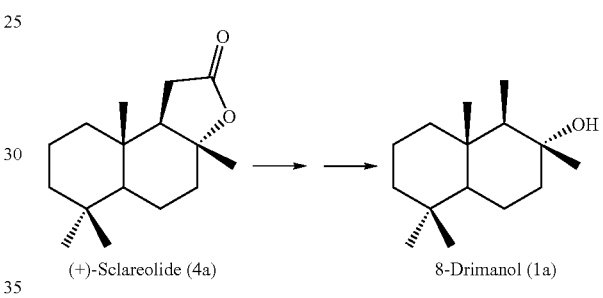

By heating (+)-sclareolide (4a) in formic acid in the presence of concentrated sulfuric acid, 9-epi-sclareolide (4c) is obtained (Non-patent Document 1). By carrying out the reaction of the present invention by using this epi-form, (9βH)-driman-8α-ol (1d) can be obtained. This compound has a hydroxy group at an equatorial position in the same manner as in 8-drimanol (1a) and has a steric structure similar to that of 8-drimanol (1a) to have an amber odor.

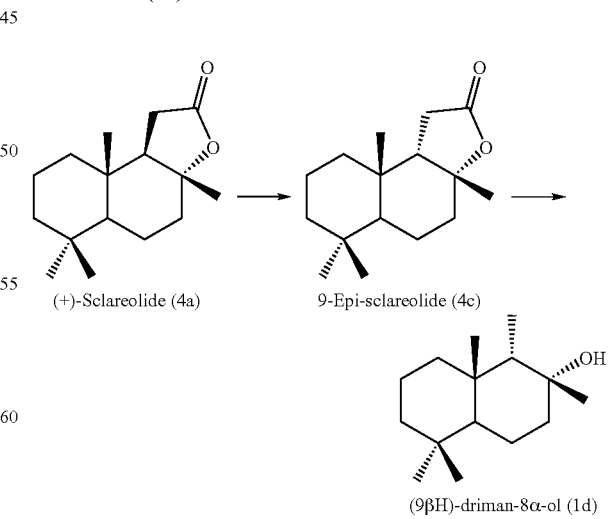

Additionally, when isosclareolide (4d) is used as sclareolide (4), driman-8β-ol (1b) is obtained.

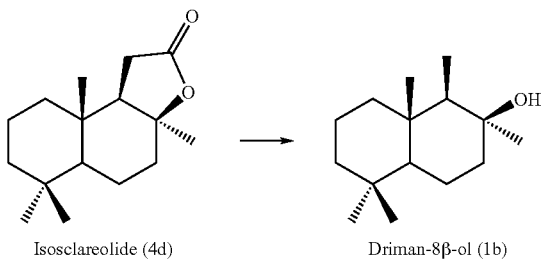

Isosclareolide (4d)    Driman-8β-ol (1b)

Further, as sclareolide (4), a mixture may also be used; a mixture containing 8-drimanol (1a) can be produced more inexpensively from (±)-sclareolide (4ab) obtained from homofarnesylic acid or the like by means of a heretofore known method (JP-A-8-506103).

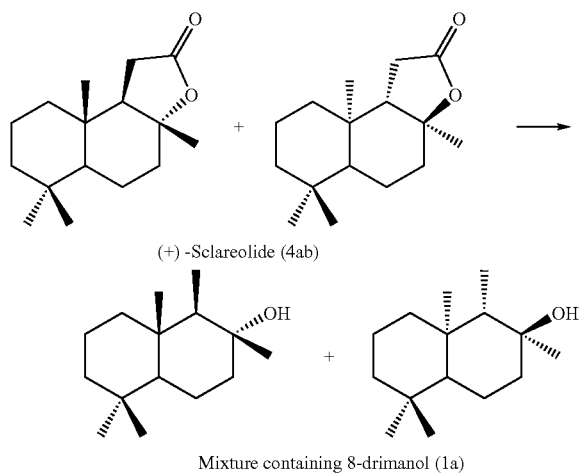

(+)-Sclareolide (4ab)

Mixture containing 8-drimanol (1a)

The component (b) is a fragrance compound, similar to the component (a), which has a decalin or octalin skeleton, or a decahydronaphthofuran skeleton; by adding the component (a), the component (b) can exhibit an effect to enhance the odor quality of the woody-amber odor without impairing the features of the component (b).

The fragrance composition of the present invention includes 0.0005 to 10% by mass of the component (a) and 90 to 99.9995% by mass of the component (b). The contents of the component (a) and the component (b) are preferably 0.001 to 10% by mass and 90 to 99.999% by mass, respectively, more preferably 0.005 to 10% by mass and 90 to 99.995% by mass, respectively, and furthermore preferably 0.01 to 10% by mass and 90 to 99.99% by mass, respectively.

Further, the fragrance composition of the present invention containing the component (a) and the component (b) can be used in combination with one or more of the following fragrance substances.

(1) Hydrocarbons such as limonene, α-pinene, β-pinene, terpinene, cedrene, longifolene and valencene.

(2) Alcohols such as linalool, citronellol, geraniol, nerol, terpineol, dihydromyrcenol, ethyl linalool, farnesol, nerolidol, cis-3-hexenol, cedrol, menthol, borneol, phenylethyl alcohol, benzyl alcohol, phenylhexanol, 2,2,6-trimethylcyclohexyl-3-hexanol, 1-(2-t-butylcyclohexyloxy)-2-butanol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol, 3-methyl-5-(2,2,3-trimethyl-3-cyclopenten-1-yl)-4-penten-2-ol, isocamphylcyclohexanol and 3,7-dimethyl-7-methoxyoctan-2-ol.

(3) Phenols such as eugenol, thymol and vanillin.

(4) Esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styrallyl acetate, cinnamyl acetate, dimethylbenzylcarbinyl acetate, 3-pentyltetrahydropyran-4-yl acetate, citronellyl propionate, tricyclodecenyl propionate, allyl cyclohexylpropionate, ethyl 2-cyclohexylpropionate, benzyl propionate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyl dihydrojasmonate, methyl 2,4-dihydroxy-3,6-dimethylbenzoate, ethylmethylphenyl glycidate, methyl anthranilate and Fultate (trade name, manufactured by Kao Corp.).

(5) Aldehydes such as n-octanal, n-decanal, n-dodecanal, 2-methylundecanal, 10-undecenal, citronellal, citral, hydroxycitronellal, dimethyltetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal and α-methyl-3,4-methylenedioxyhydrocinnamic aldehyde.

(6) Ketones such as methylheptenone, 4-methylene-3,5,6,6-tetramethyl-2-heptanone, amylcyclopentanone, 3-methyl-2-(cis-2-penten-1-yl)-2-cyclopenten-1-one, methylcyclopentenolone, rose ketone, γ-methyl ionone, α-ionone, carvone, menthone, camphor, nootkatone, benzyl acetone, anisyl acetone, methyl β-naphthyl ketone, 2,5-dimethyl-4-hydroxy-3(2H)-furanone, maltol, muscone, civetone, cyclopentadecanone and cyclohexadecenone.

(7) Acetals and ketals such as acetaldehyde ethylphenylpropylacetal, citral diethyl acetal, phenylacetaldehyde glycerinacetal and ethylacetoacetate ethylene glycol ketal.

(8) Ethers such as anethole, β-naphthyl methyl ether, β-naphthyl ethyl ether, limonene oxide, rose oxide and 1,8-cineol; and nitriles such as geranyl nitrile and citronellyl nitrile.

Further, in addition to carboxylic acids, the following lactones, and natural essential oils and natural extracts can also be used in combination with the component (a) and the component (b): lactones such as γ-nonalactone, γ-undecalactone, δ-decalactone, γ-jasmolactone, coumarin, cyclopentadecanolide, cyclohexadecanolide, ambrettolide, ethylene brassylate and 11-oxahexadecanolide; and natural essential oils and natural extracts obtained from orange, lemon, bergamot, mandarin, peppermint, spearmint, lavender, chamomile, rosemary, eucaly, sage, basil, rose, geranium, jasmine, ylang-ylang, anis, clove, ginger, nutmeg, cardamom, cedar, Japanese cypress, vetiver, patchouli and labdanum.

The fragrance composition of the present invention can be mixed in or applied to various forms of aromatic products. The application fields of the fragrance composition of the present invention include, for example, cosmetic products, household products and environmental/sanitary products.

It is to be noted that "cosmetic products" mean products to keep the personal appearance clean or fine; specific examples thereof include soaps, body-cleansing agents, hair-cleansing agents, hair cosmetics, cosmetics (for example, skin cosmetics and finish cosmetics), perfumes, colognes, antiperspirants, deodorants and bath agents.

It is to be noted that "household products" mean products to maintain the functionality and cleanliness of various articles necessary for domestic life such as houses themselves and household articles; specific examples thereof include clothes detergents, clothes softeners, clothes starch, house detergents, bath detergents, dish detergents, bleaching agents, mildew cleaners and floor waxes.

It is to be noted that "environmental/sanitary products" mean products to regulate the environment at predetermined conditions or atmospheres, in particular, products capable of regulating, by applying fragrance compositions, an odor floating in the environment; specific examples of such products include air fresheners, deodorants, incense fragrances, incense sticks and candles.

The component (a) emits a weak woody-amber-like odor at room temperature, but increases the odor intensity thereof steeply by heating, at temperatures of body temperatures or above, to develop a pleasant amber-like odor. Accordingly, the fragrance composition of the present invention can attain high olfactory effects particularly in the following products: products in the forms of direct application to the skin and hair such as perfumes, colognes, skin-care products, cosmetics, hair-care products for beautifying or styling; products having forms involving heating such as bath agents used under heated conditions, hair-care products such as shampoos and conditioners to be heated with a hair dryer after being applied; and products such as clothes finishing agents and softeners to be heated in a dryer or with an iron after being applied.

Additionally, the odor persistence behavior of the component (a) resembles that of the component (b); accordingly, even when the component (a) is combined with the component (b), the component (a) can persist of a high odor quality of the note possessed by natural ambergris without changing the odor. Consequently, by direct application to the skin or hair, a faint and soft odor can be made to persist. Additionally, household products such as clothes detergents and clothes softeners can effectively leave the odor in clothes at the time of washing or treatments. Yet additionally, the fragrance composition of the present invention tends to be matched with the fragrances used in the environmental/sanitary products such as air fresheners, deodorants, incense sticks and candles.

There are various ways of application of the products including the fragrance composition of the present invention; for example, positive applications of perfumes or cosmetics to predetermined locations to develop the odor, applications of detergents leaving the odor in the applied locations after rinsing, applications of the air fresheners to be emitted in the air so as for the odor therefrom to float in the air, and applications of incense sticks or candles to be kindled so as for the odor therefrom to float in the air.

For example, a hair-cleaning agent obtained as follows brings about an odor having warmth and a high odor quality, and can make a soft and elegant odor to persist in the hair: the component (a) is added in an amount of 0.005% by mass to the component (b), the mixture thus obtained is mixed in an amount of 20% by mass in a fragrance composition, and the fragrance composition thus obtained is added in an amount of 0.5% by mass to a hair-cleaning agent to yield the above-mentioned hair-cleaning agent.

EXAMPLES

Production Example 1

Production of 8-drimanol (1a)

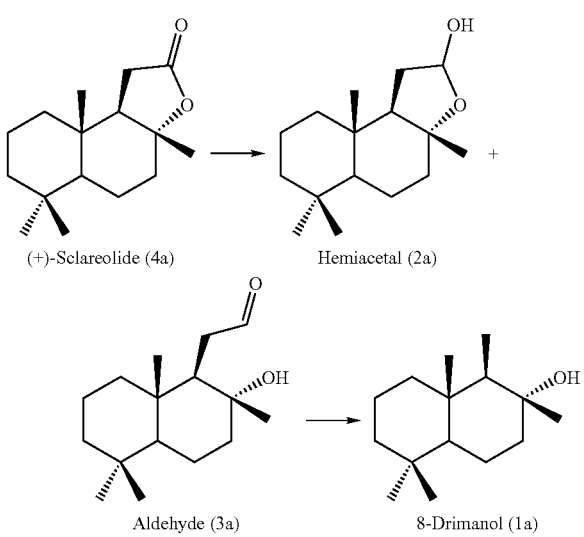

(+)-Sclareolide (4a)  Hemiacetal (2a)

Aldehyde (3a)  8-Drimanol (1a)

In a 200-mL four-necked flask equipped with a stirrer and a thermometer, 5 g of (+)-sclareolide and 60 mL of anhydrous dichloromethane were placed in a nitrogen atmosphere and cooled while stirring down to −78° C. To the solution thus prepared, 22 mL of a n-hexane solution of diisobutylaluminum hydride was slowly added dropwise by using a syringe and stirred while cooling for 25 minutes. Thereafter, 12.5 mL of a saturated aqueous solution of ammonium chloride was added slowly and the solution was heated while stirring up to room temperature. The solution was diluted with diethyl ether, then stirred for 1.5 hours, then anhydrous magnesium sulfate was added and stirred for a while, and then filtered with celite. The filtrate was concentrated by removal under reduced pressure to yield 4.75 g (yield: 95%) of a white crystal (a mixture of hemiacetal (2a) and aldehyde (3a)).

Next, 2 g of the obtained solid substance was dissolved in 320 mL of dichloromethane in a 1-L four-necked flask and stirred for a few minutes. To the solution, 7.5 g of chlorotris(triphenylphosphine)rhodium(I) was added, and the solution was stirred for 13 hours under refluxing conditions. Thereafter, the solution was made to return to room temperature, then further stirred for 30 minutes, and thereafter filtered. The filtrate was subjected to removal under reduced pressure, and then purified by silica gel column chromatography (dichloromethane:methanol=100:1 by volume) to yield 1.2 g (yield: 60%) of 8-drimanol (1a).

The compound thus obtained was identified to be 8-drimanol (1a) on the basis of the following spectra.

$^1$HNMR (400 MHz, CDCl$_3$, δ: ppm): 0.79 (3H, s), 0.80 (3H, s) 0.87 (3H, s), 0.83-0.94 (4H, m), 1.11 (3H, s), 1.13-1.31 (4H, m), 1.36-1.45 (3H, m), 1.52-1.65 (3H, m), 1.89 (1H, m)

$^{13}$CNMR (100 MHz, CDCl$_3$, δ: ppm): 7.83, 14.81, 19.09, 20.91, 22.04, 23.55, 33.63, 33.88, 38.18, 40.23, 42.28, 44.81, 55.93, 56.47, 73.35

IR [νmax (KBr): cm$^{-1}$]: 3314, 2925, 1463, 1377, 1158, 1077, 937, 722

$[\alpha]^{25}_D$ −20.9° (c 0.57, CHCl$_3$)

[Odor Evaluation]

A sheet of aluminum foil was placed on a hot plate, 0.1 g of the component (a) obtained by the above-mentioned method was placed on the sheet of aluminum foil, and the odor was evaluated while the temperature was being increased; the results obtained are as follows.

Room temperature: A weak woody odor was identified.
40° C.: Amber feeling was intensified.
50° C.: Strong amber odor with sweetness was identified.
60° C.: Extremely strong amber odor was identified.

Production Example 2

Production of 8-drimanol (1a) with a Catalyst Amount of 0.034 Equivalent

In a 300 mL four-necked flask equipped with a thermometer, a refluxing tube and a stirrer bar, 1.92 g (2.08 mmol) of chlorotris(triphenylphosphine)rhodium(I), 1.89 g (4.58 mmol) of 1,3-bis(diphenylphosphino)propane and 139 mL of dehydrated xylene were placed, and the air in the flask was replaced with nitrogen. Then, the reaction mixture was heated to an oil-bath temperature of 80° C., and heated as it was while stirring for 15 minutes. Then, to the flask, 15.36 g (60.9 mmol) of a mixture of hemiacetal (2a) and aldehyde (3a) obtained in the same manner as in Production Example 1 was added, and the reaction mixture was heated to an oil-bath temperature of 155° C., and heated under refluxing and while stirring for 9 hours. After cooling the reaction mixture, the solid substance was removed by filtration, and the filtrate was concentrated and subjected three times to silica gel column purification (hexane:ethyl acetate=5:1) to yield 6.28 g (purity: 99%, 27.8 mmol, yield: 46%) of 8-drimanol (1a).

Production Example 3

Production of 8-drimanol (1a) with a Catalyst Amount of 0.0025 Equivalent

In a 100 mL four-necked flask equipped with a thermometer, a refluxing tube and a stirrer bar, 0.139 g (0.15 mmol) of chlorotris(triphenylphosphine)rhodium(I), 0.068 g (0.165 mmol) of 1,3-bis(diphenylphosphino)propane and 10 mL of dehydrated xylene were placed, and the air in the flask was replaced with nitrogen. Then, the reaction mixture was heated to an oil-bath temperature of 80° C., and heated as it was while stirring for 15 minutes. Then, to the flask, 1.27 g (5 mmol) of a mixture of hemiacetal (2a) and aldehyde (3a) obtained in the same manner as in Production Example 1 was added, and the reaction mixture was heated to an oil-bath temperature of 155° C., and heated under refluxing and while stirring in a flow of nitrogen. After an elapsed time of 8 hours, 0.068 g (0.165 mmol) of 1,3-bis(diphenylphosphino)propane was further added to improve the reaction rate, and after a total elapsed time of 10 hours, the raw materials were identified to disappear almost completely. To the reaction mixture, 2.54 g (10 mmol) of the mixture of hemiacetal (2a) and aldehyde (3a) and 20 mL of dehydrated xylene were added, and the reaction mixture was heated at an oil-bath temperature of 155° C. under refluxing and while stirring in a flow of nitrogen. In the course of the reaction, the reaction rate was found to be decreased, and hence 0.068 g (0.165 mmol) of 1,3-bis(diphenylphosphino)propane was yet further added for the reaction rate to be recovered to the same level as in the initial stage. Such operations were repeated to use a total amount of 0.272 g (0.66 mmol) of 1,3-bis(diphenylphosphino)propane and a total mount of 60 mL of dehydrated xylene, and thus, a total amount of 15.24 g (60 mmol) of the mixture of hemiacetal (2a) and aldehyde (3a) was converted into 8-drimanol (1a) (GC yield based on internal standard: 76%).

Examples 1 to 4 and Comparative Example 1

Fragrance compositions A, B, C and D were prepared according to the mass ratios shown in Table 1, and each of the fragrance compositions was dissolved in a commercially available liquid paraffin so as to have a concentration of 1% by mass. A liquid paraffin solution of a fragrance composition E containing no component (a), prepared under the same conditions as for the above-mentioned fragrance compositions A to D, was adopted as a reference, and the comparative evaluation of odor was carried out based on the interactive discussions between four expert panelists. Consequently, as shown below, a high effect of the component (a) was identified.

<Evaluation Results>

Fragrance composition A: Warmth as well as amber feeling was imparted.

Fragrance composition B: Amber feeling and warmth were intensified, and effects to bring about voluminous feeling and cleanliness feeling were identified.

Fragrance composition C: Amber-like warmth and voluminous feeling were furthermore intensified.

Fragrance composition D: Warmth and softness were enhanced, and cosmetic and powdery feeling were slightly accentuated.

TABLE 1

| | | | Dodecahydro-3a,6,6,9a-tetramethylnaphtho[2,1-b]furan (Note) (% by mass) | Component (a) (% by mass) |
|---|---|---|---|---|
| Ex. | 1 | Fragrance Compo. A | 99.9995 | 0.0005 |
| | 2 | Fragrance Compo. B | 99.9990 | 0.0010 |
| | 3 | Fragrance Compo. C | 99.9950 | 0.0050 |
| | 4 | Fragrance Compo. D | 99.9900 | 0.0100 |
| Com. Ex. | 1 | Fragrance Compo. E | 100 | 0 |

(Note) Ambroxan (trade name, Kao Corp.) derived from a natural raw material sclareol and purified by recrystallization from ethanol to increase the purity was used.

Examples 5 and 6 and Comparative Example 2

Fragrance compositions F and G were prepared, and a fragrance H was adopted as a reference, and the comparative evaluation of odor was carried out on the basis of the interactive discussions between four expert panelists in the same manner as in Example 1. Consequently, as shown below, a high effect of the component (a) was identified.

<Evaluation Results>

Fragrance composition F: An effect was identified in which woody and fruity odor of the racemic form was modified and amber-like warmth was intensified.

Fragrance composition G: Amber-like warmth and voluminous feeling were furthermore intensified.

TABLE 2

|   |   |   | Dodecahydro-3a,6,6,9a-tetramethylnaphtho[2,1-b]furan (Note) (% by mass) | Component (a) (% by mass) |
|---|---|---|---|---|
| Ex. | 5 | Fragrance Compo. F | 99.9990 | 0.0010 |
|  | 6 | Fragrance Compo. G | 99.9900 | 0.0100 |
| Com. Ex. | 2 | Fragrance Compo. H | 100 | 0 |

(Note) Cetalox (trade name, Firmenich Co.) in racemic form was used.

Example 7

To 99.999 parts by mass of a fragrance composition having a composition shown in Table 3, 0.001 part by mass of the component (a) was added, and thus, an amber-type odor having sweetness and the features of natural ambergris was able to be obtained.

TABLE 3

| Ingredients | Parts by mass |
|---|---|
| 7-Acetyl-1,2,3,4,5,6,7,8-octahydro-1,1,6,7-tetramethylnaphthalene | 60 |
| 3a-Ethyldodecahydro-6,6,9a-trimethylnaphtho[2,1-b]furan | 10 |
| 1,2,3,4,4a,7,8,8a-Octahydro-2,4a,5,8a-tetramethyl-1-naphthyl formate | 10 |
| 1,2,3,4,4a,5,6,7-Octahydro-2,5,5-trimethyl-2-naphthalenol | 0.5 |
| Dodecahydro-3a,6,6,9a-tetramethylnaphtho[2,1-b]furan | 5 |
| Dipropylene glycol | 14.499 |
| Total | 99.999 |

Example 8

Fragrance Composition for Perfume

To 99.5 parts by mass of a fragrance composition for perfume having a composition shown in Table 4, 0.5 part by mass of the fragrance composition B of Example 2 (Table 1) was added, and thus, a fragrance composition was able to be obtained, which was characterized by having a fruity top note, and musky softness and warm sweetness, and having a bright and elegant amber-like long-lasting odor on the skin.

TABLE 4

| Ingredients | Parts by mass |
|---|---|
| Methyl dihydrojasmonate | 25 |
| 1,3,4,6,7,8-Hexahydro-4,6,6,7,8,8-hexamethylcyclopenta-γ-2-benzopyran | 15 |
| p-t-Butyl-α-methylhydrocinnamic aldehyde | 8 |
| Orange oil | 5 |
| Ethyl linalol | 4 |
| cis-3-Hexenyl salicylate | 3 |
| Ethylene brassylate | 3 |
| 4(3)-(4-Hydroxy-4-methylpentyl)-3-cyclohexene-1-carboxy aldehyde | 3 |
| Piperonal | 2 |
| Hexyl acetate | 2 |
| Citronellol | 1 |
| Phenylethyl alcohol | 1 |
| 7-Hexadecen-16-olide | 1 |

TABLE 4-continued

| Ingredients | Parts by mass |
|---|---|
| Allyl heptanoate | 1 |
| Dihydromyrcenol | 1 |
| p-t-Butylcyclohexyl acetate | 1 |
| 2-t-Butylcyclohexyl ethyl carbonate | 0.5 |
| 3,6-Dimethyl-3-cyclohexene-1-carboaldehyde | 0.2 |
| γ-Undecalactone | 0.2 |
| Styralyl acetate | 0.2 |
| n-Decanal | 0.1 |
| Rose oxide | 0.1 |
| Dipropylene glycol | 22.2 |
| Total | 99.5 |

Comparative Example 3

Fragrance Composition for Perfume

To 99.5 parts by mass of a fragrance composition for perfume of Example 8 having a composition shown in Table 4, 0.5 part by mass of the fragrance composition E of Comparative Example 1 (Table 1) was added, and thus, a fragrance composition was obtained which had an amber odor insufficiently, and an odor deficient in warmth.

Example 9

Fragrance Composition for Clothes Detergent

To 94.5 parts by mass of a fragrance composition having a composition shown in Table 5, 5.5 parts by mass of a woody-amber fragrance composition I shown in Table 6 was added, and thus, a fragrance composition for clothes detergent was obtained which brought about a sweet and soft odor.

TABLE 5

| Ingredients | Parts by mass |
|---|---|
| Orange oil | 20 |
| Methyl dihydrojasmonate | 15 |
| Linalol | 10 |
| Cyclopentadecanolide | 10 |
| p-t-Butyl-α-methylhydrocinnamic aldehyde | 10 |
| α-n-Hexylcinnamic aldehyde | 8 |
| Citronellol | 6 |
| 2-Methyl-4-(2,2,3-trimethyl-3-cyclopenten-1-yl)-2-buten-1-ol | 5 |
| Linalyl acetate | 4 |
| γ-Methyl ionone | 3 |
| o-t-Butylcyclohexyl acetate | 3 |
| Methyl β-naphthyl ketone | 0.5 |
| Total | 94.5 |

TABLE 6

| Ingredients (Fragrance composition I) | Parts by mass |
|---|---|
| Dodecahydro-3a,6,6,9a-tetramethylnaphtho[2,1-b]furan (Note) | 0.499 |
| 7-Acetyl-1,2,3,4,5,6,7,8-octahydro-1,1,6,7-tetramethylnaphthalene | 5 |
| Component (a) | 0.001 |
| Total | 5.5 |

(Note) Ambroxan (trade name, Kao Corp.) derived from a natural raw material sclareol and purified by recrystallization from ethanol to increase the purity was used.

Comparative Example 4

Fragrance Composition for Clothes Detergent

To 94.5 parts by mass of the fragrance composition of Example 9 having a composition shown in Table 5, 5.5 parts by mass of a woody-amber fragrance composition J shown in Table 7 was added, and thus, a fragrance composition for a clothes detergent was obtained which had a sufficiently perceivable woody-amber odor having some hardness and being deficient in softness and voluminous feeling.

TABLE 7

| Ingredients (Fragrance composition J) | Parts by mass |
|---|---|
| Dodecahydro-3a,6,6,9a-tetramethylnaphtho[2,1-b]furan (Note) | 0.5 |
| 7-Acetyl-1,2,3,4,5,6,7,8-octahydro-1,1,6,7-tetramethylnaphthalene | 5 |
| Total | 5.5 |

(Note) Ambroxan (trade name, Kao Corp.) derived from a natural raw material sclareol and purified by recrystallization from ethanol to increase the purity was used.

Example 10

Clothes Detergent Composition

To 99.6 parts by mass of a powder detergent composition having a composition described in Table 8, 0.4 part by mass of the fragrance composition for clothes detergent obtained in Example 9 (Table 5+Table 6) was sprayed; 20 g of the thus treated powder detergent composition was weighed out and dissolved in 30 L of 3.5° DH hard water. In the aqueous solution thus obtained, 2 kg of commercially available cotton towel was placed, and the aqueous solution was stirred for 5 minutes, and the towel was rinsed for 1 minute, and then dried. The smell of this cotton towel was evaluated; a odor having softness and cleanliness was perceived to identify an effect of the component (a).

TABLE 8

| Ingredients | Parts by mass |
|---|---|
| Sodium linear alkyl($C_{10}$-$C_{18}$)benzenesulfonate | 30 |
| Sodium alkyl($C_{12}$-$C_{16}$)sulfate | 5 |
| Polyoxyethylene (POE average addition number of moles: 6 to 15) alkyl($C_{12}$-$C_{18}$) ether | 10 |
| ($C_{14}$-$C_{20}$) Soap | 5 |
| Crystalline aluminosilicate | 25 |
| Sodium carbonate | 15.6 |
| Sodium sulfate | 6 |
| Polyethylene glycol (Molecular weight: 8,000 to 10,000) | 2 |
| Granular enzyme | 1 |
| Total | 99.6 |

Comparative Example 5 Clothes Detergent Composition

In place of the fragrance composition for clothes detergent obtained in Example 9 (Table 5+Table 6) and used in Example 10, the woody-amber fragrance composition of Comparative Example 4 (Table 5+Table 7) was used, and the smell of the cotton towel was evaluated in the same manner as in Example 10; consequently, it was found that the woody odor with some hardness was intensified to degrade the balance and the warmth and voluminous feeling possessed by natural ambergris were not identified.

Example 11

Fragrance Composition for Clothes Detergent

To 94.5 parts by mass of the fragrance composition of Example 9 having the composition shown in Table 5, 5.5 parts by mass of a woody-amber fragrance composition K shown in Table 9 was added, and thus, a fragrance composition for clothes detergent was able to be obtained which brought about a soft odor having a fruity feeling and sweetness.

TABLE 9

| Ingredients (Fragrance composition K) | Parts by mass |
|---|---|
| Dodecahydro-3a,6,6,9a-tetramethylnaphtho[2,1-b]furan (Note) | 0.499 |
| 7-Acetyl-1,2,3,4,5,6,7,8-octahydro-1,1,6,7-tetramethylnaphthalene | 5 |
| Component (a) | 0.001 |
| Total | 5.5 |

(Note) Cetalox (trade name, Firmenich Co.) in racemic form was used.

Comparative Example 6

Fragrance Composition for Clothes Detergent

To 94.5 parts by mass of the fragrance composition of Example 9 having the composition shown in Table 5, 5.5 parts by mass of a woody-amber fragrance composition L shown in Table 10 was added, and thus, it was found that a fruity feeling was accentuated to degrade the balance and warmth and a voluminous feeling were not identified.

TABLE 10

| Ingredients (Fragrance composition L) | Parts by mass |
|---|---|
| Dodecahydro-3a,6,6,9a-tetramethylnaphtho[2,1-b]furan (Note) | 0.5 |
| 7-Acetyl-1,2,3,4,5,6,7,8-octahydro-1,1,6,7-tetramethylnaphthalene | 5 |
| Total | 5.5 |

(Note) Cetalox (trade name, Firmenich Co.) in racemic form was used.

Example 12

Fragrance Composition for Clothes Softener

To 99.5 parts by mass of a fragrance composition having a composition shown in Table 11, 0.5 part by mass of the fragrance composition A of Example 1 (Table 1) was added, and thus, a fragrance composition for clothes softener was able to be obtained which was regulated in odor and had an odor with a sweetness and voluminous feeling.

TABLE 11

| Ingredients | Parts by mass |
| --- | --- |
| Orange oil | 10 |
| Tricyclodecenyl acetate | 8 |
| γ-Methyl ionone | 8 |
| Acetyl cedrene | 7 |
| Hexyl salicylate | 6 |
| Muguet-type blended fragrance | 5 |
| Rose-type blended fragrance | 5 |
| 2-Methyl-4-(2,2,3-trimethyl-3-cyclopenten-1-yl)-2-buten-1-ol | 5 |
| Phenylhexanol | 5 |
| α-n-Hexylcinnamic aldehyde | 5 |
| Methyl dihydrojasmonate | 4 |
| Phenylethyl alcohol | 4 |
| Cyclopentadecanolide | 4 |
| Ethoxymethyl cyclododecyl ether | 4 |
| p-t-Butyl-α-methylhydrocinnamic aldehyde | 3 |
| p-t-Butylcyclohexyl acetate | 3 |
| 2-t-Butylcyclohexyl ethyl carbonate | 3 |
| Jasmine-type blended fragrance | 3 |
| 4(3)-(4-Hydroxy-4-methylpentyl)-3-cyclohexene-1-carboxy aldehyde | 2 |
| Methyl β-naphthyl ketone | 2 |
| Anisaldehyde | 2 |
| Patchouli oil | 1.5 |
| Total | 99.5 |

Example 13

Clothes Softener Composition

To 99.5 parts by mass of a softener composition having a composition shown in Table 12, 0.5 part by mass of the fragrance composition obtained in Example 12 (Table 11+Example 1 in Table 1) was added; 3 g of the thus treated clothes softener composition was weighed out and dissolved in 30 L of water. In the aqueous solution thus obtained, 2 kg of commercially available cotton towel was placed, and the aqueous solution was stirred at 25° C. for 1 minute. Then, the towel was dehydrated and dried at room temperature. The next day, the smell of this cotton towel was evaluated, and thus, the following results were obtained: even in dried cloth, a musky odor, a sandal-like sent, a floral odor and an amber odor having richness and voluminous feeling were able to be perceived, and a sweet odor persisted.

TABLE 12

| Ingredients | Parts by mass |
| --- | --- |
| Distearyldimethylammonium chloride (trade name: Cotamine D86P, Kao Corp.) | 15 |
| Silicone compound | 0.01 |
| Calcium chloride | 0.05 |
| Ethanol | 2 |
| Water | 82.44 |
| Total | 99.5 |

Example 14

Fragrance Composition for Shampoo

To 99.5 parts by mass of a fragrance composition having a composition shown in Table 13, 0.5 part by mass of the fragrance composition B of Example 2 (Table 1) was added, and thus, a fragrance composition for shampoo was able to be obtained, which was characterized by having a floral odor with musky softness and having an amber-like odor with sweetness and voluminous feeling.

TABLE 13

| Ingredients | Parts by mass |
| --- | --- |
| Linalol | 15 |
| Methyl dihydrojasmonate | 13 |
| Cyclopentadecanolide | 12 |
| p-t-Butyl-α-methylhydrocinnamic aldehyde | 10 |
| cis-3-Hexenyl salicylate | 10 |
| Dimethylbenzylcarbinyl acetate | 5 |
| Phenylethyl alcohol | 5.5 |
| Citronellol | 5 |
| 1-[[2-(1,1-dimethylethyl)cyclohexyl]oxy]-2-butanol | 5 |
| α-n-Hexylcinnamic aldehyde | 4 |
| Benzyl acetate | 4 |
| 7-Acetyl-1,2,3,4,5,6,7,8-octahydro-1,1,6,7-tetramethylnaphthalene | 3 |
| Orange oil | 3 |
| Linalyl acetate | 3 |
| γ-Methyl ionone | 2 |
| Total | 99.5 |

Example 15

Fragrance Composition for Liquid Body-Cleaning Agent

To 99.7 parts by mass of a fragrance composition having a composition shown in Table 14, 0.3 part by mass of the fragrance composition C of Example 3 (Table 1) was added, and thus, a fragrance composition for liquid body-cleaning agent, which was characterized by having a long-lasting soft, warm and sweet odor on the skin.

TABLE 14

| Ingredients | Parts by mass |
| --- | --- |
| Muguet-type blended fragrance | 15 |
| Rose-type blended fragrance | 10 |
| Linalol | 8 |
| Methyl dihydrojasmonate | 8 |
| Orange oil | 5 |
| β-Ionone | 5 |
| Cyclohexyl salicylate | 5 |
| o-t-Butylcyclohexyl acetate | 5 |
| Cyclopentadecenolide | 5 |
| 1-[[2-(1,1-Dimethylethyl)cyclohexyl]oxy]-2-butanol | 4 |
| 4-Methyl-2-(2-methylpropyl)tetrahydro-2H-4-pyranol | 4 |
| Dimethylbenzylcarbinyl n-butyrate | 4 |
| Piperonal | 4 |
| Ethoxymethyl cyclododecyl ether | 3 |
| 7-Acetyl-1,2,3,4,5,6,7,8-octahydro-1,1,6,7-tetramethylnaphthalene | 3 |
| Patchouli oil | 3 |
| 2-Methyl-4-(2,2,3-trimethyl-3-cyclopenten-1-yl)-2-buten-1-ol | 3 |
| Isolongifolanone | 3 |
| γ-Undecalactone | 2.5 |
| 3a-Ethyldodecahydro-6,6,9a-trimethylnaphtho[2,1-b]furan (racemic type) | 0.2 |
| Total | 99.7 |

The invention claimed is:

1. A method for producing a decalin alcohol represented by formula (1):

(1)
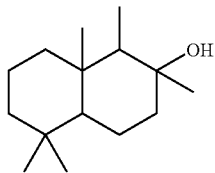

said method comprising:
(i) decarbonylating a hemiacetal compound represented by formula (2) or an aldehyde compound represented by formula (3), or a combination thereof:

(2)
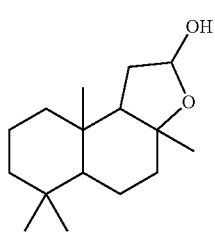

(3)
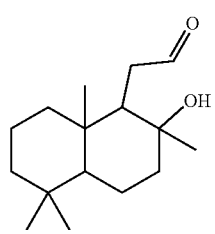

to obtain said decalin alcohol represented by formula (1), wherein said decarbonylating is carried out in the presence of a transition metal complex which is at least one member selected from the group consisting of a rhodium complex, a ruthenium complex, an iron complex, and mixtures thereof.

2. A method according to claim 1, wherein said decarbonylating is carried out in the presence of a bidentate phosphine ligand.

3. A method according to claim 2, wherein said transition metal complex is present in a catalytic amount of the complex.

4. A method according to claim 1, which comprises decarbonylating said hemiacetal compound represented by formula (2).

5. A method according to claim 4, wherein said hemiacetal compound represented by formula (2) is produced by reducing sclareolide represented by formula (4):

(4)
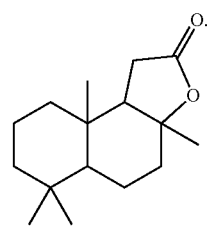

6. A method according to claim 5, comprising reducing said sclareolide represented by formula (4) with a metal hydride.

7. A method according to claim 1, which comprises decarbonylating said aldehyde compound represented by formula (3).

8. A method according to claim 7, wherein said aldehyde compound represented by formula (3) is produced by reducing sclareolide represented by formula (4):

(4)
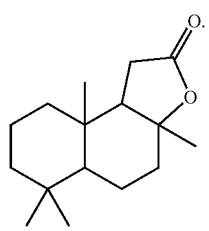

9. A method according to claim 8, comprising reducing said sclareolide represented by formula (4) with a metal hydride.

10. A method according to claim 1, which comprises decarbonylating a mixture of said hemiacetal compound represented by formula (2) and said aldehyde compound represented by formula (3).

11. A method according to claim 10, wherein said mixture of said hemiacetal compound represented by formula (2) and said aldehyde compound represented by formula (3) is produced by reducing sclareolide represented by formula (4):

(4)
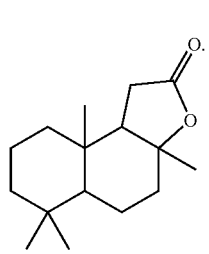

12. A method according to claim 11, comprising reducing said sclareolide represented by formula (4) with a metal hydride.

13. A method according to claim 1, wherein the decalin alcohol is 8-drimanol.

14. A method according to claim 1, wherein said decarbonylating is carried out in a single step.

15. A method according to claim 4, wherein said decarbonylating is carried out in a single step.

16. A method according to claim 7, wherein said decarbonylating is carried out in a single step.

17. A method according to claim 10, wherein said decarbonylating is carried out in a single step.

18. A method according to claim 1, wherein said transition metal complex comprises a rhodium complex.

* * * * *